(12) United States Patent
D'Amato et al.

(10) Patent No.: US 6,723,858 B2
(45) Date of Patent: Apr. 20, 2004

(54) ESTROGENIC COMPOUNDS AS ANTI-MITOTIC AGENTS

(75) Inventors: Robert John D'Amato, Lancaster, PA (US); Moses Judah Folkman, Brookline, MA (US)

(73) Assignee: The Children's Medical Center Corporation, Boston, MA (US)

( * ) Notice: Subject to any disclaimer, the term of this patent is extended or adjusted under 35 U.S.C. 154(b) by 15 days.

(21) Appl. No.: 10/080,076

(22) Filed: Feb. 21, 2002

(65) Prior Publication Data

US 2002/0119959 A1 Aug. 29, 2002

Related U.S. Application Data

(62) Division of application No. 09/243,158, filed on Feb. 2, 1999, which is a division of application No. 08/838,699, filed on Apr. 25, 1997, now Pat. No. 5,892,069, which is a division of application No. 08/571,265, filed on Dec. 12, 1995, now Pat. No. 5,661,143, which is a continuation of application No. 08/102,767, filed on Aug. 6, 1993, now Pat. No. 5,504,074.

(51) Int. Cl.[7] ............... C07D 321/00; C07D 313/00; C07D 311/78; C07D 315/00; A61K 31/56
(52) U.S. Cl. ............... 549/228; 549/346; 549/354; 549/381; 549/382; 549/383; 549/416; 549/417; 549/419; 514/182
(58) Field of Search ............... 549/228, 346, 549/354, 381, 382, 383, 416, 417, 419; 552/627, 652; 514/182

(56) References Cited

U.S. PATENT DOCUMENTS

| | | |
|---|---|---|
| 2,584,271 A | 2/1952 | Huffman |
| 2,846,453 A | 8/1958 | Hoehn |
| 3,166,577 A | 1/1965 | Ringold et al. |
| 3,410,879 A | 11/1968 | Smith et al. |
| 3,470,218 A | 9/1969 | Farah |
| 3,492,321 A | 1/1970 | Crabbe |
| 3,496,272 A | 2/1970 | Kruger |
| 3,562,260 A | 2/1971 | De Ruggieri et al. |
| 3,956,348 A | 5/1976 | Hilscher |
| 4,172,132 A | 10/1979 | Draper et al. |
| 4,212,864 A | 7/1980 | Tax |
| 4,307,086 A | 12/1981 | Tax |
| 4,522,758 A | 6/1985 | Ward et al. |
| 4,634,705 A | 1/1987 | DeBernardis et al. |
| 4,743,597 A | 5/1988 | Javitt et al. |
| 4,808,402 A | 2/1989 | Leibovich et al. |
| 4,994,443 A | 2/1991 | Folkman et al. |
| 5,001,116 A | 3/1991 | Folkman et al. |
| 5,135,919 A | 8/1992 | Folkman et al. |
| 5,504,074 A | 4/1996 | D'Amato et al. |
| 5,521,168 A | 5/1996 | Clark |
| 5,621,124 A | 4/1997 | Seilz et al. |
| 5,629,340 A | 5/1997 | Kuwano et al. |
| 5,639,725 A | 6/1997 | O'Reilly et al. |
| 5,643,900 A | 7/1997 | Fotsis et al. |
| 5,661,143 A | 8/1997 | D'Amato et al. |
| 5,716,981 A | 2/1998 | Hunter et al. |
| 5,733,876 A | 3/1998 | O'Reilly et al. |
| 5,776,704 A | 7/1998 | O'Reilly et al. |
| 5,792,845 A | 8/1998 | O'Reilly et al. |
| 5,837,682 A | 11/1998 | O'Reilly |
| 5,854,205 A | 12/1998 | O'Reilly et al. |
| 5,854,221 A | 12/1998 | Cao et al. |
| 5,861,372 A | 1/1999 | Folkman et al. |
| 5,885,795 A | 3/1999 | O'Reilly et al. |
| 5,892,069 A | 4/1999 | D'Amato et al. |
| 6,011,023 A | 1/2000 | Clark et al. |
| 6,136,992 A | 10/2000 | Ram et al. |
| 6,200,966 B1 | 3/2001 | Stewart |
| 6,239,123 B1 | 5/2001 | Green |
| 6,284,789 B1 | 9/2001 | LaLonde et al. |
| 6,399,773 B1 | 6/2002 | Liu et al. |
| 6,448,419 B1 | 9/2002 | Paaren et al. |
| 6,514,971 B1 | 2/2003 | Thomas et al. |
| 2002/0068724 A1 | 6/2002 | Slaga et al. |

FOREIGN PATENT DOCUMENTS

| | | |
|---|---|---|
| DE | 1907330 | 10/1969 |
| DE | 2 004 516 | 9/1970 |
| DE | 27 57 157 | 12/1977 |
| DE | 3625315 | 1/1988 |
| EP | 0166937 A2 | 8/1986 |
| GB | 857080 | 12/1960 |
| GB | 8578081 | 12/1960 |
| JP | 39-5480 B | 3/1964 |
| JP | 41 000100 A | 1/1966 |
| JP | 42-928 B | 1/1967 |
| JP | 58-131978 | 8/1983 |
| JP | 63090763 A | 4/1988 |
| JP | 63-119500 | 5/1988 |
| JP | 11-209322 | 1/1998 |
| SU | 1240038 A1 | 10/1996 |
| WO | WO 87/02367 A3 | 4/1987 |
| WO | WO 88/08002 A1 | 10/1988 |
| WO | WO 90/15816 A1 | 12/1990 |
| WO | WO 93/03729 | 3/1993 |

(List continued on next page.)

OTHER PUBLICATIONS

*Research Plus Catalog*, pp. 50–58, 1993.

U.S. Patent application No. 09/580,897, filed May 30, 2000 entitled "Estrogenic Compounds as Anti–Mitotic Agents".

(List continued on next page.)

*Primary Examiner*—Samuel Barts
*Assistant Examiner*—Sikarl A. Witherspoon
(74) *Attorney, Agent, or Firm*—Kilpatrick Stockton LLP

(57) ABSTRACT

The application discloses methods of treating mammalian diseases characterized by abnormal cell mitosis by administering estradiol derivatives including those comprising colchicine or combretastatin A-4 structural motifs of the general formulae found below in a dosage sufficient to inhibit cell mitosis. The application discloses novel compounds used in the methods.

15 Claims, 3 Drawing Sheets

FOREIGN PATENT DOCUMENTS

| WO | WO 95/04535 | 2/1995 |
|---|---|---|
| WO | WO 9832763 A1 | 7/1998 |
| WO | WO 98/40398 | 9/1998 |
| WO | WO 99/01142 A1 | 1/1999 |
| WO | WO 99/22728 A1 | 5/1999 |
| WO | WO 99/33858 A3 | 7/1999 |
| WO | WO 99/33859 A2 | 7/1999 |
| WO | WO 00/07576 A2 | 2/2000 |
| WO | WO 00/10552 A2 | 3/2000 |
| WO | WO 00/66095 A2 | 11/2000 |
| WO | WO 00/68246 A1 | 11/2000 |
| WO | WO 01/27132 A1 | 4/2001 |
| WO | WO 01/85755 A1 | 11/2001 |

OTHER PUBLICATIONS

Adams, E.F. et al., Steroidal regulation of oestradiol–17B dehydrogenase activity of the human breast cancer cell line MCF–7 (Chemical Abstracts Doc. No. 109:32325, 1988), *Journal of Endocrinology*, vol./Iss: 188(1), pp. 149–154, Jul. 1988.

Bhat et al., Estradiol–induced Mitotic Inhibition in the Bursa of Fabricius of Male Domestic Duckling (Chemical Abstracts Doc. No: 98:31837, 1982), *Mikroskopie*, vol./Iss: 39, pp. 113–117, May 1982.

Blickenstaff et al., Estrogen–Catharanthus (Vinca) Alkaloid Conjugates (Chemial Abstracts Doc. No:, *Cytotoxic Estrogens in Hormone Receptive Tumors*, pp. 89–105, 1980.

Boye et al., 185. Deaminocolchinyl Methyl Ether: Synthesis from 2,3,4,4'–Tetramethoxybiphenyl–2–carbaldehyde. Comparison of Antitubulin Effects of Deaminocolchinyl *Helvetica Chimica Acta*, vol./Iss: 72, pp. 1690–1696, 1989.

Brem, H. et al., Interstitial chemotherapy with drug polymer implants for the treatment of recurrent gliomas, *Journal of Neurosurgery*, vol./Iss. 74, pp. 441–446, Mar. 1, 1991.

Cohen et al., Novel Total Synthesis of (+)–Estrone 3–Methyl Ether, (+)–13B–Ethyl–3–methoxygona–1,3,5(10–triene–17–one, and (+)–Equilenin 3–Methyl Ether, *The Journal of Chemistry*, vol./Iss: 45, pp. 71–97, 1992.

Collins et al., The Structure and Function of Estrogens. XI* Synthesis of (+/−)–7(8–11α) abeo–Estradiol and its 9,11–Didehydro Derivative, *Aust. Journal of Chemistry*, vol./Iss: 45, pp. 71–97, 1992.

Crum, R. et al., A New Class of Steroids Inhibit Angiogenesis in the Presence of Heparin or a Heparin Fragment, *Science*, vol./Iss: 230, pp. 1375–1378, Dec. 20, 1985.

Evans et al., A Convergent Total Synthesis of (+)–Colchicine and (+)–Desacetamidoisocolchicine, *Journal of the American Chemical Society*, vol./Iss: 103, pp. 5813–5821, Sep. 23, 1981.

Fitzgerald, Molecular Features of Colchicine Associated with Antimitotic Activity and Inhibition of Tubulin Polymerization, *Biochemical Pharmacology*, vol./Iss: 25, pp. 1383–1387, Jun. 15, 1976.

Getahun et al., Synthesis of Alkoxy–Substituted Diaryl Compounds and Correlation of Ring Separation with Inhibition of Tubulin Polymerization: Differential Enhancement of Inhibitory Effects Under Suboptimal Polymerization Reaction Conditions, *Journal of Medical Chemistry*, vol./Iss: 35 (6), pp. 1058–1067, Mar. 20, 1992.

Gross et al., Inhibition of Tumor Growth, Vascularization, and Collagenolysis in the Rabbit Cornea by Medroxyprogesterone, *Proceedings of the National Academy of Science USA*, vol. 78 (2), pp. 1176–1180, Feb. 1981.

Hartley–Asp et al., Diethystilbestrol Induces Metaphase Arrest and Inhibits Microtubule Assembly, *Mutation Research*, vol./Iss: 143 (4), pp. 231–235, Aug. 1985.

Huber et al., Tubulin Binding of Conformationally Restricted Bis–Aryl Compounds, *Bioorganic & Medicinal Chemistry Letters*, vol./Iss. 1 (5), pp. 243–246, 1991.

Lin et al., Interactions of Tubulin with Potent Natural and Synthetic Analogs of the Antimitotic Agent Combretastatin: A Structure–Activity Study, *Molecular Pharmacology*, vol./Iss: 34 (2), pp. 200–208, Aug. 1988.

Lincoln et al., Conformation of Thiocolchicine and Two B–Ring–Modified Analogues Bound to Tubulin Studied with Optical Spectroscopy, *Biochemistry*, vol./Iss: 30 (5), pp. 1179–1187, Feb. 5, 1991.

Lottering et al., Effects of the 17β–Estradiol Metabolites on Cell Cycle Events in MCF–7 Cells (Chemical Abstracts Doc. No.: 117:245769, 1992), *Cancer Research*, vol./Iss: 52, pp. 5926–5932, Nov. 1, 1992.

Mayol et al., Ethynylestradiol–Induced Cell Proliferation in Rat Liver Involvement of Specific Populations of Hepatocytes (Abstract only), *Cancinogenesis*, vol./Iss: 12(12), pp. 2381–2388, 1992.

Morgan et al., Calcium and Oestrogen Interactions upon the Rat Thymic Lymphocyte Plasma Membrane (Chemical Abstracts Doc. No.: 85:172052, 1976), *Biochemical and Biophysical Research Communications*, vol./Iss: 72 (2), pp. 663–672, Sep. 20, 1976.

Mukundan et al., Liver Regeneration in Oral Contraceptive Treated Female Rats—Effects of Moderate Malnutrition (Chemical Abstracts Doc. No.: 102:143342, 1984), *Hormone and Metabolic Research*, vol./Iss.: 16(12), pp. 641–645, Dec. 1984.

Nakamura et al., Studies on the Total Synthesis of dl–Colchicine. I. Synthesis of 3–Hydroxy–9, 10, 11–trimethoxy–1,2,3,4,6,7–hexahydro–5H–dibenso[a,c] cycloheptatrien–5–one, *Chemical and Pharmaceutical Bulletin*, vol./Iss: 10, pp. 281–290, 1962.

Ochs et al., Effect of Tumor Promoting Contraceptive Steroids on Growth and Drug Metabolizing Enzymes in Rat Liver (Abstract only), *Cancer Research*, vol./Iss: 46 (3), pp. 1224–1232, 1986.

Oppolzer et al., 177. The Enantioselective Synthesis of (+)–Estradiol from 1,3–Estradiol from 1,3–Dihydrobenzol [c] thiopene–2,2–dioxide by Successive Thermal $SO_2$–Extrusion and Cycloaddition Reactions, *Helvetica Chimica Acta*, vol./Iss: 63, pp. 1703–1705, 1980.

Paull et al., Identification of Novel Antimitotic Agents Acting at the Tubulin Level by Computer–assisted Evaluation of Differential Cytotoxicity Data, *Cancer Research*, vol./Iss: 52, pp. 3892–3900, Jul. 15, 1992.

Poli et al., Tumur Necrosis Factor α Functions in an Autocrine Manner in the Induction of Human Immunodeficiency Virus Expression, *Proceedings of the National Academy of Science USA*, vol./Iss: 87, pp. 782–785, Jan. 1990.

Rao et al., Structural Specificity of Estrogens in the Induction of Mitotic Chromatid Non–Disjunction in Hela Cells, *Journal of Experimental Cell Research*, vol./Iss: 48, pp. 71–81, 1967.

Ravindra, R., Effect of Estradiol on the in vitro Assembly of Rat Brain Tubulin *Journal of Indian Institute of Science*, vol./Iss: 64(3), pp. 27–35, Mar. 1983.

Sakakibara et al., Effects of Diethylstilbestrol and its Methl Esters on Aneuploidy Induction and Microtubule Distribution in Chinese Hamster V79 cells, *Mutation Research*, vol./Iss: 263, pp. 269–276, Aug. 1991.

Sato et al., Effect of Estradiol and Ethynylestradiol on Microtubule Distribution in Chinese Hamster V79 Cells, *Chemical And Pharmaceutical Bulletin*, vol./Iss: 40(1), pp. 182–184, Jan. 1992.

Sato et al., Disruptive Effect of Diethylstilbestrol on Microtubules, *Gann*, vol./Iss: 75, pp. 1046–1048, Dec. 1984.

Sawada et al., Colchicine–Like Effect of Diethylstilbestrol (DES) on Mammalian Cells In Vitro, *Mutation Research*, vol./Iss: 57, pp. 175–182, Jun. 1978.

Seegers et al., Cyclic–AMP and Cyclic–GMP Production in MCF–7 Cells Exposed to Estradiol–17 Beta, Catecholestrogens and Methoxy–Estrogens in MCF–7 Cells (Meeting Abstract only), *Joint MCI–1st Symposium. Third 1st International Symposium. Biology and Therapy of Breast Cancer*, Sep. 25, 1989.

Seegers, J.C. et al., The Cytotoxic Effects of Estradiol–17B, Catecholestradiols and Methoxyestradiols on Dividing MCF–7 and HeLa Cells, *Journal of Steroid Chemistry*, vol./Iss: 32(6), pp. 797–809, 1989.

Sharp et al., Diethylstibestrol: the Binding of Effects of Diethylstilboestrol upon the Polymerisation and Depolymerisation of Purified Microtubule Protein in vitro, *Carcinogenesis*, vol./Iss: 6(6), pp. 865–871, Jun. 1985.

Spicer et al., Catecholestrogens Inhibit Proliferation and DNA Synthesis of Porcine Granulosa Cells in Vitro: Comparison with Estradiol, 5α–dihydrotestosterone, Gonadotropins and Catecholamines (Chemical Abstracts Doc. No.:, *Molecular and Cellular Endocrinology*, vol./Iss: 64, pp. 119–126, 1989.

Sternlicht et al., Colchicine of Microtubule Assembly via Copolymer Formation, *The Journal of Biological Chemistry*, vol./Iss: 254(20), pp. 10540–10550, Oct. 25, 1979.

Sun et al., Antitumor Agents. I39. Synthesis and Biological Evaluation of Thiocolchicine Analogs 5,6–Dihydro–6(S)–(acyloxy)–and 5,6–Dihydro–6(S)–[(acyloxy)methyl]–1,2, 3–trimethoxy–9–(methylthio)–8H–cyclohepta[a] naphthalene–8–ones as Novel Cytotoxic, *Journal of Medicinal Chemistry*, vol./Iss: 36, pp. 544–551, Mar. 5, 1993.

Sunagawa et al., Synthesis of Colchicine, Synthesis of dl–'Demethyoxydeoxy–hexahydrocolchicine, *Chemical & Pharmaceutical Bulletin*, vol./Iss: 9, pp. 81–83, 1961.

Tsutsui et al., Comparison of Human Versus Syrian Hamster Cells in Culture for Induction of Mitotic Inhibition, Binucleation and Multinucleation, Following Treatment with Four Aneuploidogens, *Toxicology in Vitro*, vol./Iss: 4(1), 75–84, 1990.

Van Tamelen et al., The Synthesis of Colchicine, *Tetrahedron*, vol./Iss: 14, pp. 8–34, Sep. 1961.

Wheeler et al., Mitotic Inhibition and Aneuploidy Induction by Naturally Occurring and Synthetic Estrogens in Chinese Hamster Cells in Vitro, *Mutation Research*, vol./Iss: 171, pp. 31–41, 1986.

Wheeler et al., Mitotic Inhibition and Chromosome Displacement Induced by Estradiol in Chinese Hamsters Cells (Chemical Abstracts Doc. No.: 105:54822, 1986), *Cell Motility and the Cytoskeleton*, vol./Iss: 7(3), pp. 235–247, 1987.

*Dictionary of Drugs (1990), Dict. of Steroids (1991), Dict. of Org. Cmpds (6th Ed) (1996), Dict. of Pharm Agents (1997)*, Lilopristone/(1–[4–(Dimethylamino)phenyl]–17–hydroxy–17–(3–hydroxy–1–propenyl) estra–4, 9–diene–3–one; AK 98734.

*The Merck Index 11th Edition*, (paragraphs 583–584), p. 88, 1989.

*Chemical Abstracts*, Registry No.: 56933–77–8.
*Chemical Abstracts*, Registry No.: 56933–78–9.
*Chemical Abstracts*, Registry No.: 57380–15–1.
*Chemical Abstracts*, Registry No.: 71782–94–0.
*Chemical Abstracts*, Registry No.: 71782–95–1.
*Chemical Abstracts*, Registry No.: 101277–11–6.
*Chemical Abstracts*, Registry No.: 101429–40–7.
*Chemical Abstracts*, Registry No.: 162853–20–5.
*Chemical Abstracts*, Registry No.: 19521–72–3, Feb. 6, 2003.

*Genetic Engineering News*, News Article: Hoffman–La Roche Signs $70 Million Deal with Millenium on Genomics Technology, Apr. 15, 1994.

*Genetic Engineering News*, News Article: Advanced Drug Delivery Systems Peak Interest of Pharmaceutical & Biotech Firms, Apr. 15, 1994.

*Genetic Engineering News*, News Article: Nasal Spray for Treating Bleeding Disorders, Apr. 15, 1994.

Aboulwafa et al., *Steroids*, Synthesis and evaluation for uterotrophic and antiimplantation activities of 2–substituted estradiol derivatives, vol. 57, pp. 199–204, Apr. 1992.

Aizu–Yokota et al., *Cancer Research*, Natural Estrogens Induce Modulation of Microtubules in Chinese Hamster V79 Cells in Culture, vol. 55, pp. 1863–1868, May 1, 1995.

Algire, G.H. et al., *Journal of the National Cancer Institute*, Vascular reactions of normal and malignant tumors in vivo. I. Vascular reactions of mice to wounds and to normal and neoplastic transplants, vol. 6, pp. 73–85, Aug. 1945.

Aliev et al., *Chemical Abstracts*, 54929q Synthesis of cycloalkyl derivatives of dihydric phenols and their ethers, vol. 72, p. 370, 1970.

Anstead et al., *Steroids*, The Estradiol Pharmacophore: Ligand Structure–Estrogen Receptor Binding Affinity Relationships and a Model for the Receptor Binding Site, vol. 62, pp. 268–303, 1997.

Arnoldi et al., *Journal of Agric. Food Chem.*, Sweet Isovanillyl Derivatives: Synthesis and Structure–Taste Relationships of Conformationally Restricted Analogs (Abstract only)vol.: 46(10), pp. 4002–1010, 1998.

Attalla et al., *Biochemical and Biophysical Research Communications*, 2–Methoxyestradiol Arrests Cells in Mitosis without Depolymerizing Tubulin, vol. 228, pp. 467–473, 1996.

Attalla et al., *Biochemical and Biophysical Research Communications*, 2–Methoxyestradiol–Induced Phosphorylation of Bcl–2: Uncoupling from JNK/SAPK Activation (Abstract only), vol. 247 (3), pp. 616–619, Jun 29, 1998.

Audier et al., *Bulletin de la Societe Chimique de France*, Orientation de la fragmentation en spectrometrie de masse par introduction de groupements fonctionnels. VII. –Etheylenecetals de ceto–2 steroides, vol. 10, pp. 3088–3090, 1965.

Ayala et al., *Shock*, The Induction of Accelerated Thymic Programmed Cell Death During Polymicrobial Sepsis: Control by Corticosteroids but not Tumor Necrosis Factor (Abstract only), vol. 3 (4), pp. 259–267, Apr. 1995.

Banik et al., *Steroids*, Orally Active Long–Acting Estrogen (AY–20,121) (3–(2–propynyloxy)–estra–1,3,5, (10)–triene–17. beta.–ol trimethylacetate) (Identifier only), vol. 16(3), pp. 289–296, 1970.

Bardon et al., *Cancer Research*, Steroid Receptor–Mediated Cytotoxicity of an Antiestrogen and an Antiprogestin in Breast Cancer Cells (Abstract only), vol. 47 (5), pp. 1441–1448, Mar. 1, 1987.

Barnes et al., *Infection and Immunity*, Tumor Necrosis Factor Production in Patients with Leprosy, vol. 60 (4), pp. 1441–1446, Apr. 1992.

Bindra et al., *Journal of Medicinal Chemistry*, Studies in Antifertility Agents.8.Seco Steroids. 2. 5,6–Secoestradiol and Some Related Compounds, vol. 18 (9), pp. 921–925, 1975.

Blagosklonny et al., *Cancer Research*, Raf–1/bcl–2 Phosphorylation: A Step from Microtubule Damage to Cell Death, vol. 57, pp. 130–135, Jan. 1, 1997.

Blickenstaff et al., *Steroids*, Synthesis of some Analogs of Estradiol, vol. 46 (4,5), pp. 889–902, Oct. 1985.

Boyce et al., *Unknown* Some Preliminary Synthetical Studies with 5,6,7,8–Tetra–hydro–8–methylindane–1,5–dione, pp. 4547–4553, 1960.

Brandi et al., *Calcif. Tissue Int.*, Bone endothelial cells as estrogen targets (Abstract only), vol. 53 (5), pp. 312–317, 1993.

Brodie, A.M., *Journal of Steroid Biochemistry and Molecular Biology*, Aromatase Inhibitors in the Treatment of Breast Cancer (Abstract only), vol. 49 (4–6), pp. 281–287, Jun. 1994.

Brosens et al., *Laboratory for Gynecological Physiopathology*, Comparative Study of the Estrogenic Effect of Ethinylestradiol and Mestranol on the Endometrium, vol. 14 (6), pp. 679–685, Dec. 1, 1976.

Brueggemeier et al., *Journal of Steroid Biochemistry & Molecular Biology*, 2–Methoxymethylestradiol: a new 2–methoxy estrogen analog that exhibits antiproliferative activity and alters tubulin dynamics, vol. 78, pp. 145–156, 2001.

Burrows, N.P., *British Medical Journal*, Thalidomide Modifies Disease, vol. 307 (6909), pp. 939–940, Oct. 9, 1993.

Cambie et al., *Journal of the Chemical Society*, Aromatic Steroids. Part II. Chromium Trioxide Oxidation of Some Oestra–1,3–5(10)–trienes, vol. 9, pp. 1234–1240, 1969.

Cambie et al., *J. Chem. Soc.*, Aromatic Steroids. Part I. Oxidation Products of 3–Methoxyestra–1,3, 5(10)–triene–17β–yl Acetate, pp. 2603–2608, 1968.

Castagnetta, L. et al., *Journal of Chromatography*, Simple Approach to Measure Metabolic Pathways of Steroids in Living Cells, vol. 572, pp. 25–39, Dec. 6, 1991.

Chasserot–Golaz et al., *Biochemical Pharmacology*, Biotransformation of 17.beta.–hydroxy–11.beta.– (4–dimethylaminophenyl)17.alpha.1–propynyl–estra–4,9– diene–3–one (RU486) in Rat Hepatoma Variants (Identifier only), vol. 46 (11), pp. 2100–2103, 1993.

Chen et al., *Steroids*, A New Synthetic Route to 2–and 4–Methoxyestradiols by Nucleophilic Substitution, vol. 47 (1), pp. 63–66, Jan. 1986.

Chen et al., *Nanjing Yaoxueyuan Xuebao*, Synthesis of 11. beta.–(4–dimethylaminophenyl)–17.beta.–hydroxy–17.alpha.–(1–propynl) estra–4, 9–dien–3–one (RU486) (Identifier only), vol. 17 (4), pp. 282–285, 1986.

Corey et al., *Tetrahedron Letters*, Applications of N,N–Dimethylhydrazones to Synthesis. Use in Efficient, Positionally and Stereochemically Selective C–C Bond Formation; Oxidative Hydrolysis to Carbonyl Compounds, vol. 1, pp. 3–6, 1976.

Corey et al., *Tetrahedron Letters*, Facile Conversion of N, N–Dimethylhydrazones to Cabonyl Compounds by Cupric Ion–Catalyzed Hydrolysis, vol. 41, pp. 36678–3668, 1976.

Crabbe, P., *Chem. Ind.*, Cotton effect of the styrene chromophore (Abstract only), vol. 27, pp. 917–918, 1969.

Cummings et al., *The American Journal of Surgical Pathology*, Apoptosis, vol. 21 (1), pp. 88–101, 1997.

Cushman et al., *Journal of Medicinal Chemistry*, Synthesis, Antitubulin and Antimitotic Activity, and Cytotoxicity of Analogs of 2–Methoxyestradiol, an Endogenous Mammalian Metabolite of Estradiol that Inhibits Tubulin Polymerization by Binding to the Colchicine Binding Site, vol. 38 (12), pp. 2041–2049, Jun. 9, 1995.

Cushman et al., *Journal of Medicinal Chemistry*, Synthesis of Analogs of 2–Methoxyestradiol with Enhanced Inhibitory Effects on Tubulin Polymerization and Cancer Cell Growth, vol. 40 (15), pp. 2323–2334, 1997.

D'Amato et al., *Proceedings of the National Academy of Science USA*, 2–Methoxyestradiol, an Endogenous Mammalian Metabolite, Inhibits Tubulin Polymerization by Interacting at the Colchicine Site, vol. 91, pp. 3964–3968, Apr. 1994.

D'Amato, R.J. et al., *Proceedings of the National Academy of Science USA*, Thalidomide is an Inhibitor of Angiogenesis, vol. 91, pp. 4082–4085, Apr. 1, 1994.

Ding et al., *Endocrinology*, Sex Hormone–Binding Globulin Mediates Prostate Androgen Receptor Action via a Novel Signaling Pathway (Abstract only), vol. 139 (1), pp. 213–218, 1998.

Dubey et al., *Biochemical and Biophysical Research Communications*, Methoxyestradiols Mediate the Antimitogenic Effects of Estradiol on Vascular Smooth Muscle Cells via Estrogen Receptor–Independent Mechanisms, vol. 278, pp. 27–33, 2000.

Durani et al., *Journal of Steroid Biochemistry*, Seco–Oestradiols and Some Non–Steroidal Oestsrogens: Structural Correlates of Oestrogenic Action, vol. 11, pp. 67–77, 1979.

Dvir et al., *Journal of Chromatography*, Thin–layer Chromatography of DANSYL–oestrogens, vol. 52, pp. 505–506, Nov. 4, 1970.

Eder et al., *Chem. Ber.*, Synthese von Ostradiol (in German– No translation available), vol. 109, pp. 2948–2953, 1976.

El–Tombary, *Arch. Pharm. Pharm. Med. Chem.*, Synthesis, Uterotropic, And Antiuterotrophic ActivitiesfoSome Estradiol Derivatives Containing Thiadiazole, Thiazoline, ad Thiazolidinone Moieties, vol. 330 (9–10), pp. 295–302, 1997.

Emons et al., *Focus MHL* Modulation der hypophysaren Sekretion von Luteinsierendem Hormon (LH) durch Ostrogene, vol. 3, pp. 221–228, 1986.

Epe et al., *Mechanisms of Chromosome Distribution and Aneuploidy*, Microtubular Proteins as Cellular Targets for Carcinogenic Estrogens and Other Carcinogens, pp. 345–351, 1989.

Fanchenko et al., *Byull. Eksp. Biol. Med.* Characteristics of the guinea pig uterus receptor system (Abstract only), vol. 85 (4), pp. 467–470, 1978.

Fetizon et al., *Bull. Soc. Chim. FR.* Synthesis of 2–keto steroids (Abstract only), vol. 8, pp. 3301–3306, 1968.

Fevig et al., *Journal of Organic Chemistry*, A Short, Stereoselective Route to 16α(Substituted–alkyl)estradiol Derivatives, vol. 52, pp. 247–251, 1987.

Field et al., *Nature*, Effect of Thalidomide on the Graft versus Host Reaction, vol. 211 (5055), pp. 1308–1310, Sep. 17, 1966.

Fieser et al., *Organic Synthesis Collective Volume 3*, N–Methylformanilide, vol. 3, pp. 590–591.

Fishman, J., *Journal of the American Chemical Society*, Synthesis of 2–Methoxyestrogens, vol. 80, pp. 1213–1216, Mar. 5, 1998.

Flohe et al., *Arzneimitte/Forschung (Germany West)*, Studies on the Hypothetical Relationship of Thalidomide–induced Embryopathy and Collagen Biosynthesis.

Folkman et al., *Science*, Angiogenesis Inhibition and Tumor Regression Caused by Heparin or a Heparin Fragment in the Presence of Cortisone, vol. 221, pp. 719–725, Aug. 19, 1983.

Folkman, J., *New England Journal of Medicine* Tumor Angiogenesis: Therapeutic Implications, vol. 285 (21), pp. 1182–1186, Nov. 18, 1971.

Folkman, J. et al., *Nature*, Induction of Angiogenesis During the Transition from Hyperplasia to Neoplasia, vol. 339, pp. 58–61, May, 4, 1989.

Folkman, J. et al., *Annals of Surgery*, Tumor Behavior in Isolated Perfused Organs in vitro Growth and Metastases of Biopsy Material in Rabbit Thyroid and Canine Intestinal Segment, vol.: 164(3), pp. 491–502, Sep. 1, 1966.

Fotsis et al., *Nature*, The Endogenous Oestrogen Metabolite 2–Methoxyoestradiol Inhibits Angiogenesis and Suppresses Tumor Growth, vol. 368, pp. 237–239, Mar. 17, 1994.

Fraser et al., *British Medical Bulletin*, Angiogenesis and its control in the female reproductive system (Abstract only), vol. 56 (3), pp. 787–797, 2000.

Gadosy et al., *Journal of Physical Chemistry*, Generation, Characterization, and Deprotonation of Phenol Radical Cations, vol. 103, pp. 8834–8839, 1999.

Gandhi et al., *Journal of Indian Chem. Soc.*, Mannich reaction of estrone, vol. 39, pp. 306–308, 1962.

Gaslini et al., *Journal of Organic Chemistry*, Reaction of Eugenol with Synthesis Gas. Synthesis of 5,6,7,8–Tetrahydro–3–methoxy–2–napthol, vol. 29(5), pp. 1177–1180, May 1964.

Gimbrone, M.A. et al., *Journal of the National Cancer Institute*, Tumor Growth and Neovascularization: An Experimental Model Using the Rabbit Cornea, vol. 52(2), pp. 413–427, Feb. 1974.

Gimbrone, M.A. et al., *Journal of Experimental Medicine*, Tumor dormancy in vivo by Prevention of Neovascularization, vol. 136, pp. 261–276, 1972.

Gonzalez et al., *Steroids*, Synthesis and Pharmacological Evaluation of 8αEstradiol Derivatives, vol. 40 (2) pp. 171–187, Sep. 1982.

Gross, J.L. et al., *Proceedings of the American Association of Cancer Research*, Modulation of Solid Tumor Growth in vivo by bFGF ( Abstract only), vol. 31, p. 79, Mar. 1990.

Gunzler, V., *Medical Hypothesis*, Thalidomide–A Therapy for the Immunological Consequences of HIV infection? vol. 30 (2), pp. 105–109, Oct. 1989.

Gupta et al.,, *Indian Journal of Chemistry*, Antifertility Agents. XIV. Secosteroids. VII. Synthesis of 2αand 2β, 6β–dimethyl–3β–(p–hyroxyphenyl)–trans–bicyclo[4.3.0] nonan–7–ones and some related compounds (Abstract only)., vol. 13 (7), pp. 759–760, 1975.

Gupta et al., *Indian Journal of Chemistry* Studies in Antifertility Agents. Part XVIII. 2o6β–Diethyl–3–β–(p–hydroxyphenl)–trans–bicyclo[4.3.0] nonan–7β–ol and 6β–methyl–3β–(p–hydroxphenyl)–2α–propyl–trans–bicyclo[4.3.0]nonan–7β–ol (Abstract only) vol.: 19B(10) pp. 886–890, 1980.

Gutierrez–Rodriguez et al., *The Journal of Rheumatology*, Treatment of Refractory Rheumatoid Arthritis –The Thalidomide Experience, vol. 16 (2), pp. 158–163, Feb. 1989.

Gutierrez–Rodriguez, O. *Arthritis and Rheumatism*, Thalidomide –A Promising New Treatment for Rheumatoid Arthritis, vol. 27, (10), pp. 1118–1121, Oct. 1984.

Hahnel et al., *Journal of Steroid Biochemistry*, The Specificity of the Estrogen Receptor of Human Uterus, vol. 4, pp. 21–31, 1973.

Haldar et al., *Cancer Research*, Bc12 is the Guardian of Microtubule Integrity, vol. 57, pp. 229–233, Jan. 15, 1997.

Hamel et al., *Biochemistry*, Interactions of 2–Methoxyestradiol, an Endogenous Mammalian Metabolite, with Unpolymerized Tubulin and with Tubulin Polymers (Abstract only), vol. 35 (4), pp. 1304–1310, 1996.

Han et al., *Journal of Biological Chemistry*, Dehydroepiandrosterone and Dihydrotestosterone Recognition by Human Estrogenic 17β–Hydroxysteroid Dehydrogenase, vol. 275 Iss 2, pp. 1105–1111, Jan 14, 2000.

Handley et al., *British Journal of Dermatology*, Chronic bullous disease of childhood and ulcerative colitis, vol. 127 (40), pp. 67–68, Jul. 1, 1992.

He et al., *Bioorganic & Medicinal Chemistry Letters*, A Versatile Synthesis of 2–Methoxyestradiol, an Endogenous Metabolite of Estradiol which Inhibits Tubulin Polymerization by Binding to the Colchicine Biding Site, vol. 4 (14), pp. 1724–1728, 1994.

He et al., *Bioorganic & Medicinal Chemistry Letters* Novel Cytokine Release Inhibitors, PartII Steroids, vol. 8, pp. 2825–2828, 1998.

Hejaz et al., *Journal of Medicinal Chemistry*, Synthesis and Biological Activity of the Superestrogen (E)–17–Oximino–3–0–sulfamolyl–1,3,5(10)–estratriene: X–ray Crystal Structure of (E)–17–Oximino–3–hydroxy–1, 3,5(10)–estratriene, vol. 42 (16), pp. 3188–3192, 1999.

Heney et al., *British Journal of Haematology*, Thalidomide treatment for chronic graft–versus–host disease, vol. 78 (1), pp. 23–27, May 1991.

Holker et al., *J. Chem. Soc. Perkin Trans.*, The Reactions of Estrogens with Benzeneseleninic Anhydride and Hexamethyldisilazane, vol. I, pp. 1915–1918, 1982.

Hori, A. et al., *Cancer Research*, Suppression of Solid Tumor Growth by Immunoneutralizing Monoclonal Antibody Against Human Basic Fibroblasts Growth Factor, vol. 51, pp. 6180–6184, Nov. 15, 1991.

Hu, G., *Proceedings of the National Academy of Sciences, USA*, Neomycin inhibits angiogenin–induced angiogenesis (Abstract only), vol. 95 (17), pp. 9791–9795, 1998.

Huang et al., *Nature*, Superoxide Dismutase as a Target for the Selective Killing of Cancer Cells (Abstract only), vol. 407 (6802), pp. 390–395, Sep. 21, 2000.

Ikegawa et al., *Biomed. Chromatogr.* Immunoaffinity extraction for liquid chromatographic determination of equilin and its metabolites in plasma (Abstract only), vol. 10 (2), pp. 73–77, 1996.

Imamura et al., *USPATFULL76:20259 US 3,950,437*, Method for Manufacture of Dihydric Phenol (Abstract only), Apr. 13, 1976.

Ingber, D. et al., *Nature*, Synthetic analogues of fumagillin that inhibit angiogenesis and suppress tumor growth, vol. 348, pp. 555–557, Dec. 6, 1990.

Iriarte et al., *Tetrahedron*, Steroids (XCIV). Synthesis of 2–methyl and 1,2–dimethyl estrogens (Abstract only), vol. 3. pp. 28–36, 1958.

Jaggers et al., *Journal of Endocrinology*, Potent Inhibitory effects of steroids in an in vitro model of angiogenesis (Abstract only), vol. 150 (3), pp. 457–464, 1996.

Jhingran et al., *Steroids*, Studies in Antifertility agents –Part XLI: Secosteroids–x: Syntheses of Various Stereoisomers of (+–)–2, 6β–diethyl–7α–ethynyl–3–(p–hydroxyphenyl)–trans–bicyclo 4.3.0)nonan–7β–ol., vol. 42(6), pp. 627–634, 1983.

Josefsson et al., *Arthritis & Rheumatism*, Suppression of Type II Collagen–Induced Arthritis by the Endogenous Estrogen Metabolite 2–Methoxyestradiol, vol. 40 (1), pp. 154–163, Jan. 1997.

Kabarity et al., *Mutation Research*, Further Investigations on the cytological effects of some contraceptives, vol. 135, pp. 181–188, 1984.

Karwat, *Caplus DE 1103310*, Separation and Recovery of Hydrogen Sulfide from Hydrocarbon Mixture, Sep. 2, 1959.

Kataoka et al., *Cancer Research* An Agent that Increases Tumor Suppressor Transgene Product Coupled with Systemic Transgene Delivery Inhibits Growth of Metastic Lung Cancer in Vivo (Abstract only)., vol. 58 (21) pp. 4761–4765, Nov. 1998.

Kelly et al., *Journal of Clinical Endocrinology Metabolism*, The Stimulation of Prostaglandin Production by Two Antiprogesterone Steroids in Human Endometrial Cells (Abstract only)., vol. 62 (6), pp. 1116–1123, Jun. 1986.

Kim, K.J. et al., *Nature*, Inhibition of Vascular Enthdothelial Growth Factor–induced Angiogenesis Suppresses Tumor Growth in Vivo, vol. 362, pp. 841–844, Apr. 29, 1993.

Klauber et al., *Cancer Research*, Inhibition of Angiogenesis and Breast Cancer in Mice by the Microtubule Inhibitors 2–Methoxyestradiol and Taxol vol. 57 pp. 81–86 Jan. 1, 1997.

Knighton, D. et al., *British Journal of Cancer*, Avascular and Vascular Phases of Tumor Growth in the Chick Embyo, vol. 35, pp. 347–356, 1977.

Kole et al., *Journal of Medicinal Chemistry*, Studies in Antifertility Agents. 11. Secosteroids.5.Synthesis of 9,11–Secoestradiol vol. 18 (7) pp. 765–766, 1975.

Kousteni et al., *Science*, Reversal of Bone Loss in Mice by Nongenotypic Signaling of Sex Steroids 298, pp. 843–846, Oct. 25, 2002.

Kovacs et al., *Acta Phys. Chem.* Steroids. XXIII. Synthesis of 2–and 4–hydroxy and 2, 4–dihydroxy derivatives of estrone and estradiol (Abstract only), vol. 19 (3), pp. 287–290, 1973.

Kurebayashi et al., *Oncology*, Paradoxical hormone responses KPL–1 breast cancer cells in vivo: a significant role of angiogenesis in tumor growth (Abstract only), vol. 59 (2), pp. 158–165, 2000.

La Vallee et al., *Cancer Research*, 2–Methoxyestradiol Up–Regulates Death Receptor 5 and Induces Apoptosis through Activation of the Extrinsic Pathway, vol. 63, pp. 468–475, Jan. 15, 2003.

Lebras, J. et al., *Organometallics*, Activation and Regioselective Ortho–Functionalization of the A–Ring of B–Estradiol Promoted by "Cp*Ir": An Efficient Organometallic Procedure for the Synthesis of 2–Methoxyestradiol, vol. 16, pp. 1765–1771, 1997.

Lewis, Richard J., *Hawley's Condensed Chemical Dictionary*, p. 577, Jan. 1993.

Lewis, Richard J., *Hawley's Condensed Chemical Dictionary*, pp. 128–129, Jan 1993.

Lichtenauer et al., *Deutsches medizinisches Journal*, Zur Behandlung des Prostata–Karzinoms, vol. 23, pp. 248–249, Jan 1972.

Lien, W. et al., *Surgery*, The blood supply of experimental liver metastases. II. A Microcirculatory study of the normal and tumor vessels of the liver with the use of perfused silicone rubber, vol. 68 (2), pp. 334–340, Aug. 1970.

Limantsev et al., *Akush Jinekol.*, Effect of some estrogen structural analogs on the development of the mouse embryo (Abstract only), vol. 6, pp. 55–56, 1982.

Lippert et al., *Life Sciences*, The effects of A–ring and D–ring metabolites of estradiol on the proliferation of vascular endothelial cells, vol. 67, pp. 1653–1658, 2000.

Liu et al., *Tetrahedron Letters*, Total Synthesis of (+–) – $\Delta^{9(12)}$–Capnellene, vol. 26 (40), pp. 4847–4850, 1985.

Loozen et al., *Recl.:J.R. Neth. Chem. Soc.*, An Approach to the synthesis of 7.beta.–amino estrogens (Abstract only), vol. 102 (10), pp. 433–437, 1983.

Lottering et al., *Cancer Letters*, 17β–Estradiol Metabolites Affect Some Regulators of the MCF–7 Cell Cycle, vol. 110, pp. 181–186, 1996.

Lovely et al., *Journal of Medicinal Chemistry*, 2–(Hydroxyalkyl)estradiols: Synthesis and Biological Evaluation, vol., 39, pp. 1917–1923, 1996.

Luo et al., *Chemical Abstracts*, Effect of Components of Crowth Ether Copper(I)Iodine Mixed Catalyst on Nuleophilic Substitution of Bromoestrogen (Abstract No. 195225), vol. 111 (21), p. 818. Col. 1, Nov. 20, 1989.

MacCarthy–Morrogh et al., *Cancer Research*, Differential Effects of Estrone and Estrone–3Θ–Sulfamate Derivatives on Mitotic Arrest, Apoptosis, and Microtubule Assembly in Human Breast Cancer Cells, vol. 60, pp. 5441–5450, Oct. 1, 2000.

Maro et al., *Journal of Embryology and Experimental Morphology*, Mechanism of Polar Body Formation in the Mouse Oocyte: An Interaction Between the Chromosome, the Cytoskeleton and the Plasma Membrane, vol. 92, pp. 11–32, 1986.

Meikrantz et al., *Journal of Cellular Biochemistry*, Apoptosis and the Cell Cycle, vol. 58 (2), pp. 160–174, Jun. 1995.

Meza et al., *Drug Therapy*, Managing the Gastrointestinal Complications of AIDS, vol. 23 (11), pp. 74–83, Nov. 1993.

Michel et al., *Biochem. Pharmacol.*, Inhibition of synaptosomal high–affinity uptake of dopamine and serotonin by estrogen agonists and antagonist (Abstract only), vol. 36 (19), pp. 3175–3180, 1987.

Miller et al., *Journal of Medicinal Chemistry*, Synthesis and Structure–Activity Profiles of A–Homoestranes, the Estratropones, vol. 40, pp. 3836–3841, 1997.

Miller, Thomas, *Dissertations Abstracts International*, Tubulin as a Therapeutic Target (Abstract only), vol. 5907B, p. 3454, 1998.

Morisaki et al., *Chem. Pharm. Bull.*, Steroids. L1. Aromatization reaction of the cross–conjugated dienone system by Zinc 9. (Abstract only), vol. 14 (8), pp. 866–872, 1966.

Mueck et al., *Journal of Clincal and Basic Cardiology*, Angiogenetic and anti–angiogenetic effects of estradiol and its metabolites (Abstract only), vol. 4 (2) pp. 153–155, 2001.

Mukhopadhyay et al., *Oncogene*, Induction of Apoptosis in Human Lung Cancer Cells after Wild–Type p53 Activation by Methoxyestradiol, vol. 14, pp. 379–384, 1997.

Naafs et al., *International Journal of Dermatology*, Thalidomide Therapy An Open Trial, vol. 24 (2), pp. 131–134, Mar. 1985.

Nakagawa–Yagi et al., *Life Sciences*, The Endogenous Estrogen Metabolite 2–Methoxyestradiol Induces Apoptotic Neuronal Cell Death In Vitro, vol. 58 (17), pp. 1461–1467, 1996.

Nambara et al., *Chem. Pharm. Bulletin*, Studies on Steroid Conjugates. III. New Synthesis of 2–Methoxyestrogens, vol. 18 (3), pp. 474–480, Mar. 1970.

Nambara et al., *Chem. Pharm. Bull.*, Microbial transformation products derived from steriods. I. Synthesis of 1,2–and 3–dimethoxy–4–methylestratienes (Abstract only), vol. 20 (2), pp. 336–342, 1972.

Nambara et al., *Chemical & Pharmaceutical Bulletin*, Synthesis of 16β–Oxygenated Catechol Estrogen Methyl Ethers, New and Potential Metabolites, vol. 23 (7), pp. 1613–1616, Jul. 1975.

Napolitano et al., *Journal of Medicinal Chemistry*, 11 Beta–Substituted Estradiol Derivatives. 2. Potential Carbon–11 and Iodine–Labeled Probes for the Estrogen Receptor (Abstract only), vol. 38 (14), pp. 2774–2779, Jul. 7, 1995.

Newkome et al., *Journal of Organic Chemistry*, Synthesis of Simple Hydrazones of Carbonyl Compounds by an Exchange Reaction, vol. 31, pp. 677–681, Mar. 1966.

Nguyen, M. et al., *Journal of the National Cancer Institute*, Elevated Levels of the Angiogenic Peptide Basic Fibroblast Growth Factor in Urine of Bladder Cancer Patients, vol. 85 (3), pp. 241–242, Jan. 3, 1993.

Nishigaki et al., *Atherosclerosis*, Anti–Proliferative Effect of 2–Methoxyestradiol on Cultures Smooth Muscle Cells from Rabbit Aorta, vol. 113, pp. 167–170, 1995.

Numazawa et al., *Journal of the Chemical Society*, Efficient Synthesis of 2–Methoxy–and 4–Methoxy–Estrogens, pp. 533–534, Jan. 1, 1983.

Numazawa et al., *Steroids*, Novel and Regiospecific Synthesis of 2–Amino Estrogens via Zincke Nitration, vol. 41 (5), pp. 675–682, 1983.

Omar et al., *European Journal of Medicinal Chemistry*, Synthesis, binding affinities and uterotrophic activity of some 2–substituted estradiol and ring–A–fused pyrone derivatives, vol. 29, pp. 25–32, 1994.

Pakala et al., *European Journal of Pharmacology*, Modulation of Endothelial Cell Proliferation by Retinoid x Receptor Agonists, vol. 385 (2/3), pp. 255–261, Sep. 1999.

Parthasarathy et al., *Journal of Clinical Investigation*, Antioxidant: A New Role for RU–486 and Related Compounds (Abstract only), vol. 94 (5), pp. 1990–1995, Nov. 1994.

Peng et al., *Journal of the American Chemical Society*, Synthesis and Optical Properties of Novel Unsymmetrical Conjugated Dendrimers, vol. 122, pp. 6619–6623, 2000.

Pert et al., *Australian Journal of Chemistry*, Preparations of 2, 4–disubstituted estradiols (Abstract only), vol. 42 (3), pp. 421–432, 1989.

Peters et al., *Journal of Medicinal Chemistry*, 17–Desoxy Estrogen Analogues, vol. 32 (7), pp. 1642–1652, 1989.

Pfeiffer et al., *Journal of Endocrinology*, Are catechol estrogens obligatory mediators of estrogen action in the central nervous system? I. Characterization of pharmacological probes with different receptor binding affinities and catechol estrogen formation rates (Abstract only), vol. 110 (3), pp. 489–497, 1986.

Powell et al., *British Journal of Dermatology*, Investigation and Treatment of Orogenital Ulceration; studies on a Possible Mode of Action of Thalidomide, vol. 113 Supp. 28, pp. 141–144, Jul. 1985.

Pribluda et al., *The New Angiotheraphy*, 2–Methoxyestradiol –A Novel Endogenous Chemotherapeutic and Antiangiogenic Agent–Chapter 21, pp. 1–21, Nov. 2000.

Rao et al., *Synthesis*, A Novel, Two–Step Synthesis of 2–Methoxyestradiol, pp. 168–169, Mar. 1, 1977.

Romanelli et al., *Organic Synthesis*, Ethyl–ρ– Dimethylaminophenylacetate, vol. 5, p. 552.

Sakakibara, Kyoichi, *Chemical Abstracts*, 2–Hydroxy–1,3, 5(10)–estratriene derivatives (Abstract only) (Identifier: XP–002186126), vol. 60(1), Jan. 6, 1964.

Sato et al., *Horm. Carcinog. II. Proceedings Int. Symp., 2nd (1996), Meeting Date 1994*, Natural estrogens induce modulation of microtubules in Chinese hamster V79 cells in culture (Abstract only), pp. 454–457, 1996.

Seegers et al. *Journal of Steroid Biochemistry and Molecular Biology*, The Mammalian Metabolite, 2–methoxyestradiol, Affects P53 Levels and Apoptosis Induction in Transformed Cells but Not in Normal Cells (Abstract only), vol. 62 (4), pp. 253–267, Jul. 1997.

Shah et al., *Journal of Medicinal Chemistry*, (+/–)–(N–alkylamino)benzazepine Analogs: Novel Dopamine D1 Receptor Antagonists, vol. 38 (21), pp. 4284–4293, Oct. 13, 1995.

Shim et al., *Caplus: Bioorganic & Medicinal Chemistry*, Hydrazinocurcumin, A Novel Synthetic Curcumin Derivative, Is a Potent Inhibitor of Endothelial Cell Proliferation (Abstract only), vol. 10 (8), pp. 2439–2444, 2002.

Shishkina et al., *Khim.–Farm. Zh.*, Synthesis and properties of condensed heterocylic derivatives of estra–4, 9–dien–17. beta.–ol–3–one (Abstract only), vol. 8 (1), pp. 7–11, 1974.

Sidky et al., *Cancer Research*, Inhibition of Angiogenesis by Interferons: Effects on Tumor–and Lymphocyte–induced Vascular Responses, vol. 47, pp. 5155–5161, Oct. 1, 1987.

Singh et al., *Molecular and Cellular Endocrinology*, Inhibition of deoxyglucose uptake in MCF–7 breast cancer cells by 2–methoxyestrone and 2–methoxyestrone– 3–Θ–sulfamate (Abstract only), vol. 160 (1–2), pp. 61–66, 2000.

Siracusa et al., *Jouranl of Embryology and Experimental Morphology*, The effect of microtubule–and microfilament – disrupting drugs on preimplantation mouse embryos ( Abstract only), vol. 60, pp. 71–82, Dec. 1980.

Spyriounis et al., *Arch. Pharm.*, Copper (II) complex of an estradiol derivative with potent antiinflammatory properties (Abstract only), vol. 324 (9) pp. 533–536, 1991.

Srivastava, A. et al., *American Journal of Pathology*, The Prognostic Significance of Tumor Vascularity in Immediate–Thickness (0.76–4.0 mm Thick) Skin Melanoma, vol. 133 (2), pp. 419–424, Nov. 1988.

Starkov et al., *Zhumal Prikladnoi Khimii*, Mono–and Dialkylation of Guaiacol by Olefins on KU–2 Cation Exchanger (Abstract only), vol. 41 (3) pp. 688–690, 1968.

Taylor, S. et al., *Nature*, Protamine is an Inhibitor of Angiogenesis, vol. 297, pp. 307–312, May 27, 1982.

Teranishi, M. et al., *Chemical and Pharmaceutical Bulletin*, Methylation of Catechol Estrogen with Diazomethane, vol. 31 (9), pp. 3309–3314, Sep. 1983.

Tishler et al., *Cancer Research*, Microtubule–Active Drugs Taxol, Vinblastine, and Nocodazole Increase the Levels of Transcriptionally Active p53., vol. 55, pp. 6021–6025, Dec. 15, 1995.

Tremblay et al., *Synthetic Communications*, A Convenient Synthetic Method for Alpha–Alkylation of Steroidal 17–Ketone: Preparatopion of 16β–(THPO–Heptyl)–Estradiol, vol. 25 (16), pp. 2483–2495, 1995.

Tremblay et al., *Bioorganic & Medicinal Chemistry*, Synthesis of 16–(Bromoalkyl)–Estradiols Having Inhibitory Effect on Human Placental Estradiol 17β–Hydroxysteroid Dehydrogenase (17β–HSD Type 1), vol. 3 (5), pp. 505–523, 1995.

Utne et al., *Journal of Organic Chemistry*, The Synthesis of 2–and 4–Fluoroestradiol, vol. 33 (6), pp. 2469–2473, Jun. 1968.

Van Geerestein et al., *Acta Crystallogr., Sect. C: Cryst. Struct. Commun.*, Structure of 11.beta.–(4–(dimethylamino)phenyl)–17.beta.–hydroxy–17.alpha.–(2–propenyl) estra–4,9–dien–3–one (Identifier only), vol. C43 (2), pp. 319–322, 1987.

Vicente et al., *Archives of Internal Medicine*, In Vitro Activity of Thalidomide Against Mycobacterium avium Complex, vol. 153 (4), p. 534, Feb. 22, 1993.

Wang et al., *Shengwu Huaxue Zazhi*, Photoaffinity labeling of human placental estradiol 17. beta.–dehydrogenase with 2–and 3–azidoestrone, 2–and 4–azidoestradiol (Abstract only), vol. 8 (6), pp. 715–718, 1992.

Wang et al., *Journal of Medicinal Chemistry*, Synthesis of B–Ring Homologated Estradiol Analogues that Modulate Tubulin Polymerization and Microtubule Stability, vol. 43, pp. 2419–2429, 2000.

Wang, Z. et al., *Synth. Commun.*, An Optimized Synthesis of 2–Methoxyestradiol, a Naturally Occurring Human Metabolite with Anticancer Activity, vol. 28 (23), pp. 4431–4437, 1998.

Weidner, N. et al., *Journal of the National Cancer Institute*, Tumor angiogenesis: A New Significant and Independent Prognostic Indicator in Early–Stage Breast Carcinoma, vol. 84, pp. 1875–1887, Dec. 16, 1992.

Weidner, N. et al., *American Journal of Pathology*, Tumor Angiogensis Correlates with Metastasis in Invasive Prostrate Carcinoma, vol. 143 (2), pp. 401–409, Aug. 1993.

Weidner, N. et al., *New England Journal of Medicine*, Tumor Angiogenesis and Metastasis–Correlation in Invasive Breast Carcinoma, vol. 324 (1), pp. 1–8, Jan. 3, 1991.

Welsch et al., *Experientia.*, Staphylostatic Activity of Some New Diphenols, Napthols, and Chalcones (Abstract only), vol. 11, pp. 350–351, 1955.

White et al., *The New England Journal of Medicine*, Treatment of Pulmonary Hemangiomatosis with Recombinant Interferon Alfa–2a, vol. 32 (18), pp. 1197–1200, May 4, 1989.

Wiese et al., *Journal of Medicinal Chemistry*, Induction of the Estrogen Specific Mitogenic Response of MCF–7 Cells by Selected Analogues of Estradiol–17 β: A 3D QSAR Study, vol. 40, pp. 3659–3669, 1997.

Wurtz et al., *Journal of Medicinal Chemistry*, Three–Dimensional Models of Estrogen Receptor Ligand Binding Domain Complexes Based on Related Crystal Structures and Mutational and Structure–Activity Relationship Data, vol. 41, pp. 1803–1814, 1998.

Yue et al., *Molecular Pharmacology*, 2–Methoxyestradiol, an Endogenous Estrogen Metabolite, Induces Apoptosis in Endothelial Cells and Inhibits Angiogenesis: Possible Role for Stress–Activated Protein Kinase Signaling Pathway and Fas Expression, vol. 51, pp. 951–952, 1997.

Zoubine et al., *International Journal of Oncology*, 2–Methoxyestradiol–Induced Growth Suppression and Lethality in Estrogen–Resposive MCF–7 Cells May Be Mediated by Down Regulation of p34cdc2 and Cyclin B1 Expression (Abstract only), vol. 15 (4), pp. 639–646, Oct. 1999.

ESTROGENIC COMPOUNDS AS ANTI-MITOTIC AGENTS

CROSS REFERENCE TO PRIOR RELATED CASES

This application is a divisional of U.S. application Ser. No. 09/243,158 filed Feb. 2, 1999, which is a divisional of U.S. application Ser. No. 08/838,699 filed Apr. 25, 1997, now U.S. Pat. No. 5,892,069, which is a divisional of U.S. application Ser. No. 08/571,265 filed Dec. 12, 1995, now U.S. Pat. No. 5,661,143, which is a continuation of application Ser. No. 08/102,767, filed Aug. 6, 1993, now U.S. Pat. No. 5,504,074. Each of the above-referenced applications is incorporated herein in its entirety.

BACKGROUND OF THE INVENTION

This invention relates to treating disease states characterized by abnormal cell mitosis.

Cell mitosis is a multi-step process that includes cell division and replication (Alberts, B. et al. In *The Cell*, pp. 652–661 (1989); Stryer, E. *Biochemistry* (1988)). Mitosis is characterized by the intracellular movement and segregation of organelles, including mitotic spindles and chromosomes. Organelle movement and segregation are facilitated by the polymerization of the cell protein tubulin. Microtubules are formed from $\alpha$ and $\beta$ tubulin polymerization and the hydrolysis of guanosine triphosphate (GTP). Microtubule formation is important for cell mitosis, cell locomotion, and the movement of highly specialized cell structures such as cilia and flagella.

Microtubules are extremely labile structures that are sensitive to a variety of chemically unrelated anti-mitotic drugs. For example, colchicine and nocadazole are anti-mitotic drugs that bind tubulin and inhibit tubulin polymerization (Stryer, E. *Biochemistry* (1988)). When used alone or in combination with other therapeutic drugs, colchicine may be used to treat cancer (WO-9303729-A, published Mar. 4, 1993; J 03240726-A, published Oct. 28, 1991), alter neuromuscular function, change blood pressure, increase sensitivity to compounds affecting sympathetic neuron function, depress respiration, and relieve gout (*Physician's Desk Reference*, Vol. 47, p. 1487, (1993)).

Estradiol and estradiol metabolites such as 2-methoxyestradiol have been reported to inhibit cell division (Seegers, J. C. et al. *J. Steroid Biochem.* 32, 797–809 (1989); Lottering, M-L. et al. *Cancer Res.* 52, 5926–5923 (1992); Spicer, L. J. and Hammond, *J. M. Mol. and Cell. Endo.* 64, 119–126 (1989); Rao, P. N. and Engelberg, *J. Exp. Cell Res.* 48, 71–81 (1967)). However, the activity is variable and depends on a number of in vitro conditions. For example, estradiol inhibits cell division and tubulin polymerization in some in vitro settings (Spicer, L. J. and Hammond, J. M. *Mol. and Cell. Endo.* 64, 119–126 (1989); Ravindra, R., *J. Indian Sci.* 64 (c) (1983)), but not in others (Lottering, M-L. et al. *Cancer Res.* 52, 5926–5923 (1992); Ravindra, R., *J. Indian Sci.* 64 (c) (1983)). Estradiol metabolites such as 2-methoxyestradiol will inhibit cell division in selected in vitro settings depending on whether the cell culture additive phenol red is present and to what extent cells have been exposed to estrogen. (Seegers, J. C. et al. Joint NCI-IST Symposium. Biology and Therapy of Breast Cancer. Sep. 25, Sep. 27, 1989, Genoa, Italy, Abstract A 58).

Numerous diseases are characterized by abnormal cell mitosis. For example, uncontrolled cell mitosis is a hallmark of cancer. In addition, cell mitosis is important for the normal development of the embryo, formation of the corpus luteum, wound healing, inflammatory and immune responses, angiogenesis and angiogenesis related diseases.

SUMMARY OF THE INVENTION

I have discovered that certain compounds within the scope of the general formulae set forth below in the claims are useful for treating mammalian diseases characterized by undesired cell mitosis. Without wishing to bind myself to any particular theory, such compounds generally inhibit microtubule formation and tubulin polymerization and/or depolymerization. Compounds within the general formulae having said inhibiting activity are preferred. Preferred compositions may also exhibit a change (increase or decrease) in estrogen receptor binding, improved absorbtion, transport (e.g. through blood-brain barrier and cellular membranes), biological stability, or decreased toxicity. I have also discovered certain compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neovascular glaucoma and Osler Weber syndrome. Other undesired angiogenesis involves normal processes including ovulation and implantation of a blastula. Accordingly, the compositions described above can be used to block ovulation and implantation of a blastula or to block menstruation (induce amenorrhea).

Other features and advantages of the invention will be apparent from the following description of preferred embodiments thereof.

COMPOUNDS ACCORDING TO THE INVENTION

As described below, compounds that are useful in accordance with the invention include novel estradiol derivatives that bind tubulin, inhibit microtubule formation or exhibit anti-mitotic properties. Specific compounds according to the invention are described below.

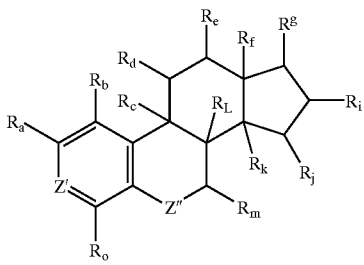

wherein:

I. $R_a$—$R_o$ are defined as follows:

A) each $R_a$, $R_b$, $R_c$, $R_d$, $R_e$, $R_f$, $R_i$, $R_j$, $R_k$, $R_L$, $R_m$, $R_o$, independently is —$R_1$, —$OR_1$, —$OCOR_1$, —$SR_1$, —F, —$NHR_2$, —Br, or —I; and $R_g$ is —$R_1$, —$OR_1$, —$OCOR_1$, —$SR_1$, —F, —$NHR_2$, —Br, —I, or —C≡CH; or B) each $R_a$, $R_b$, $R_c$, $R_f$, $R_k$, $R_L$, $R_O$, independently is —$R_1$, —$OR_1$, —$OCOR_1$, —$SR_1$, —F, —$NHR_2$, —Br, or —I; and each $R_d$, $R_e$, $R_i$, $R_j$, $R_m$, independently is =O, —$R_1$, —$OR_1$, —$OCOR_1$, —$SR_1$, —F, $NHR_2$, —Br or —I; and $R_g$ is =O, —$R_1$, —$OR_1$, —$OCOR_1$, —$SR_1$, —F, —$NHR_2$, —Br, —I, or —C≡CH; and II $Z'$ is defined as follows:

A) $Z'$ is X, where X is >$COR_1$,

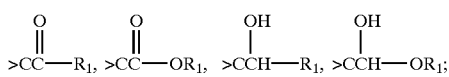

B) $Z'$ is

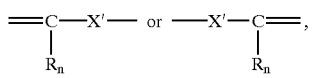

where $R_n$ is —$R_1$, —$OR_1$, —$SR_1$, —F, —$NHR_2$, —Br or —I;

and $X'$ is X, as defined above; or $X'$ is >C=O; and

III. $Z''$ is defined as follows:

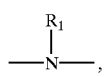

A) $Z''$ is Y, where Y is —O—, —N—,

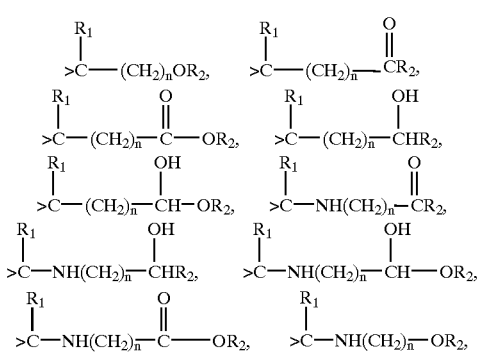

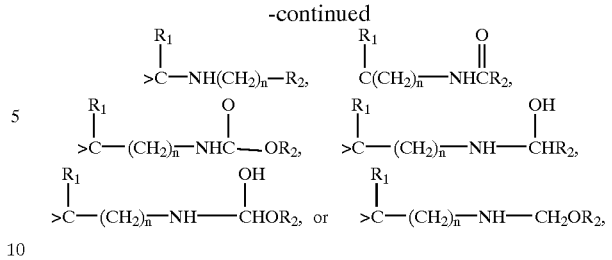

where n is 0–6

B) $Z''$ is

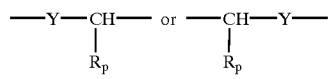

where Rp is —$R_1$, $OR_1$, —$SR_1$, —F, —$NHR_2$, —Br or —I and Y is defined as in III(A); and IV. provided that when each $R_b$, $R_c$, $R_d$, $R_e$, $R_i$, $R_j$, $R_k$, $R_L$, $R_m$ and $R_o$ is H
$R_f$ is —$CH_3$;
$R_g$ is —OH;
$Z'$ is >COH; and
$Z''$ is >$CH_2$;
then $R_a$ is not —H;

where, in each formula set forth above, each $R_1$ and $R_2$ independently is —H, or a substituted or unsubstituted alkyl, alkenyl or alkynyl group of up to 6 carbons. Those skilled in the art will appreciate that the invention extends to other compounds within the formulae given in the claims below, having the described characteristics. These characteristics can be determined for each test compound using the assays detailed below and elsewhere in the literature.

Figure 3:
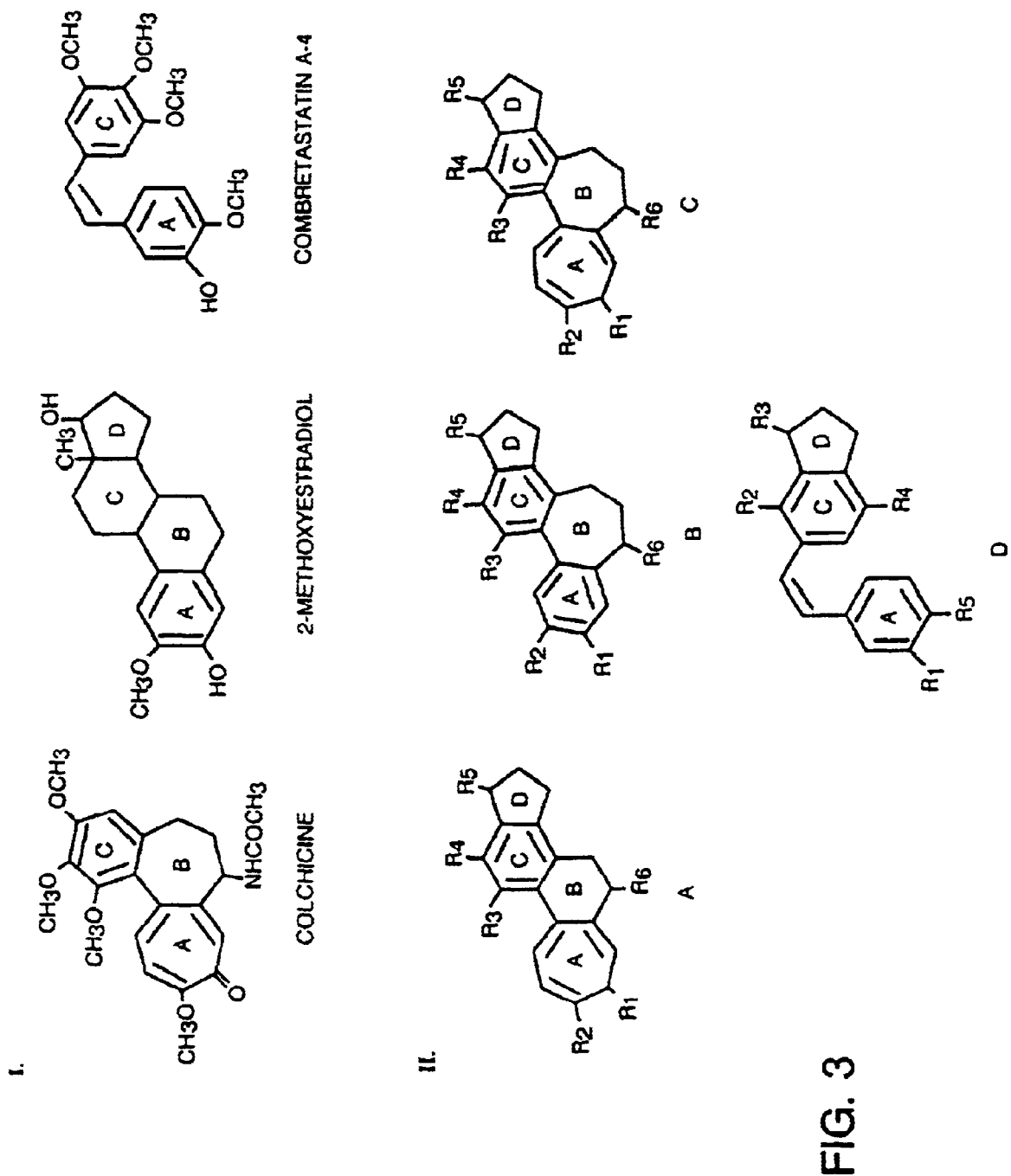
FIG. 3 depicts: I. colchicine, 2-methoxyestradiol and combretastatin A-4, and II. various estradiol derivatives comprising colchicine (a-c) or combretastatin A-4 (d) structural motifs as described below.

Without wishing to bind myself to specific mechanisms or theory, it appears that certain compounds that are known to inhibit microtubule formation, bind tubulin and exhibit anti-mitotic properties such as colchicines and combretastatin A-4 share certain structural similarities with estradiol. FIG. 3 illustrates the molecular formulae of estradiol, colchicines, combretastatin A-4, and improved estradiol derivatives that bind tubulin, inhibit microtubule assembly and exhibit anti-mitotic properties. Molecular formulae are drawn and oriented to emphasize structural similarities between the ring structures of colchicines, combretastatin A-4, estradiol, and certain estradiol derivatives. Estradiol derivatives are made by incorporating colchicines or combretastatin A-4 structural motifs into the steroidal backbone of estradiol.

FIG. 3, part I, depicts the chemical formulae of colchicine, 2-methoxyestradiol and combretastatin A-4. FIG. 3, part IIa–d, illustrates estradiol derivatives that comprise structural motifs found in colchicine or combretastatin A-4. For example, part IIa–c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 3, may be fully saturated as found in 2-methoxyestradiol. $R_{1-6}$ represent a subset of the substitution groups found in the claims. Each $R_1 \rightarrow R_6$ can independently be defined as —$R_1$, $OR_1$, —$OCOR_1$, —$SR_1$, —F, —$NHR_2$, —Br, —I, or —C≡CH.

DETAILED DESCRIPTION OF THE INVENTION

Anti-mitotic Activity In Situ

Anti-mitotic activity is evaluated in situ by testing the ability of an improved estradiol derivative to inhibit the proliferation of new blood vessel cells (angiogenesis). A suitable assay is the chick embryo chorioallantoic membrane (CAM) assay described by Crum et al. *Science* 230:1375 (1985). See also, U.S. Pat. No. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 mg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and angiogenesis.

Anti-Mitotic Activity In Vitro

Anti-mitotic activity can be evaluated by testing the ability of an estradiol derivative to inhibit tubulin polymerization and microtubule assembly in vitro. Microtubule assembly is followed in a Gilford recording spectrophotometer (model 250 or 2400S) equipped with electronic temperature controllers. A reaction mixture (all concentrations refer to a final reaction volume of 0.25 $\mu$l) contains 1.0M monosodium glutamate (ph 6.6), 1.0 mg/ml (10 $\mu$M) tubulin, 1.0 mM $MgCl_2$, 4% (v/v) dimethylsulfoxide and 20–75 $\mu$M of a composition to be tested. The 0.24 ml reaction mixtures are incubated for 15 min. at 37° C. and then chilled on ice. After addition of 10 $\mu$l 2.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 nm. Alternatively, inhibition of microtubule assembly can be followed by transmission electron microscopy as described in Example 2 below.

Indications

The invention can be used to treat any disease characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neuroscular glacoma and Oster Webber syndrome.

Improved Estradiol Derivative Synthesis

Known compounds that are used in accordance with the invention and precursors to novel compounds according to the invention can be purchased, e.g., from Sigma Chemical Co., St. Louis, Steroloids and Research Plus. Other compounds according to the invention can be synthesized according to known methods from publicly available precursors.

The chemical synthesis of estradiol has been described (Eder, V. et al., *Ber* 109, 2948 (1976); Oppolzer, D. A. and Roberts, D. A. *Helv. Chim. Acta.* 63, 1703, (1980)). Synthetic methods for making seven-membered rings in multicyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. *Tetrahedran* 14, 8–34 (1961); Evans, D. E. et al. *JACS* 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (*The Merck Index,* 11th Ed., Merck & Co., Inc., Rahway, N.J. U.S.A. (1989), pp. 583–584).

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441–446 (1991).

The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents conventional in the art having regard to the type of formulation in question, for example, those suitable for oral administration may include flavoring agents.

EXAMPLE 1

Figure 1:
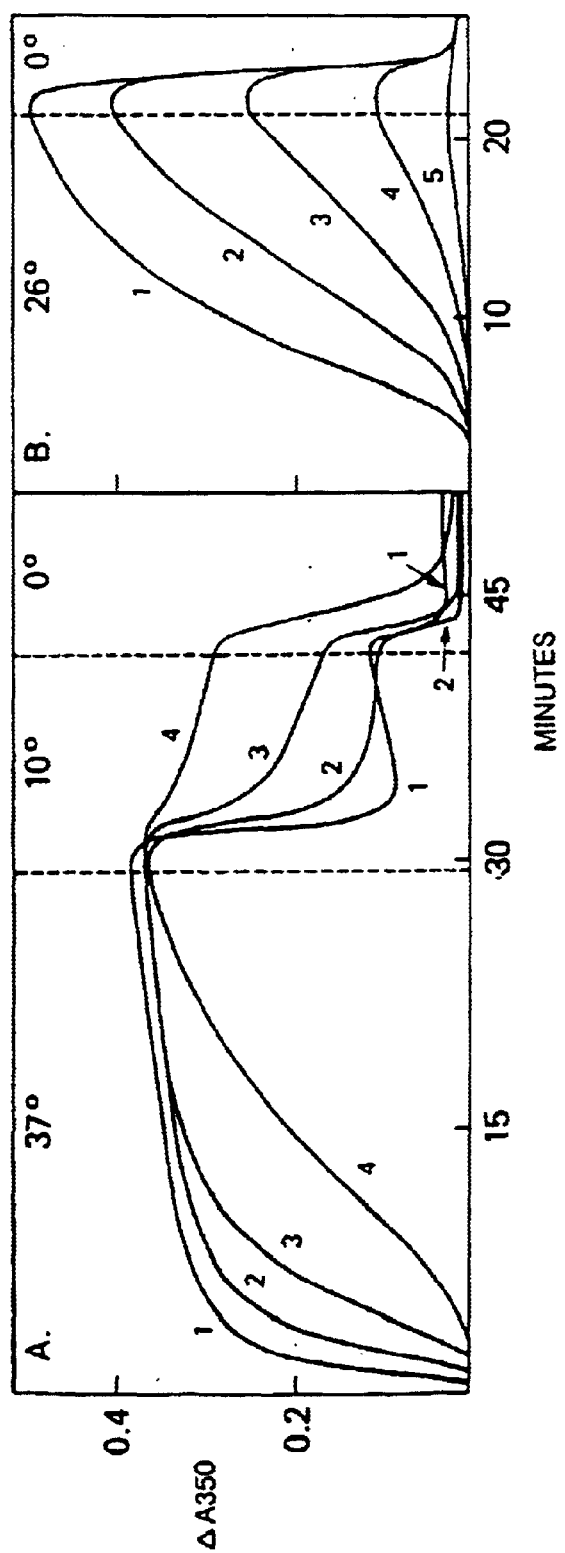
FIG. 1 is a graph illustrating the inhibition of tubulin polymerization by 2-methoxyestradiol described by Example 1 below.

FIG. 1 illustrates the inhibition of tubulin polymerization by 2-methoxyestradiol.

A. Each reaction mixture (all concentrations refer to the final reaction volume of 0.25 ml) contained 1.0 M monosodium glutamate (pH 6.6), 1.0 mg/ml (10 $\mu$M) tubulin, 1.0 mM MGCl$_2$, 4% (v/v) dimethylsulfoxide, and either 0 (curve 1), 20 $\mu$M (curve 2), 40 $\mu$M (curve 3), or 75 $\mu$M (curve 4) 2-methoxyestradiol. The 0.24 ml reaction mixtures were incubated for 15 min at 37° C. and chilled on ice. After addition of 10 $\mu$l of 2.5 mM GTP the reaction mixtures were transferred to cuvettes held at 0° C., and baselines were established. At time zero the temperature controller was set at 37° C. At the times indicated by the vertical dashed lines the temperature controller was set at the indicated temperatures.

B. Each reaction mixture contained 0.8 M monosodium glutamate (pH 6.6), 1.2 mg/ml (12 $\mu$M) tubulin, 4% (v/v) dimethylsulfoxide, and either 0 (curve 1), 1.0 $\mu$M (curve 2), 2.0 $\mu$M (curve 3), 3.0 $\mu$M (curve 4), or 4.0 $\mu$M (curve 5) 2-methoxyestradiol. The 0.24 ml reaction mixtures were incubated for 15 min at 26° C. and chilled on ice. After addition of 10 $\mu$l of 10 mM GTP the reaction mixtures were transferred to cuvettes held at 0° C., and baselines were established. At time zero the temperature controller was set at 26° C. At the time indicated by vertical dashed line the temperature controller was set at 0° C.

EXAMPLE 2

Transmission electron microscopy (TEM) can show differences between the morphology of polymerized tubulin formed in the absence or presence of 2-methoxyestradiol. After a 30 min incubation (37° C.) of reaction mixtures containing the components described in Example 1, 75 $\mu$M 2-methoxyestradiol was added, and aliquots were placed on 200-mesh carbon coated copper grids and stained with 0.5% (w/v) uranyl acetate. TEM magnifications from 23,100X to 115,400X were used to visualize differences in tubulin morphology.

EXAMPLE 3

Figure 2:
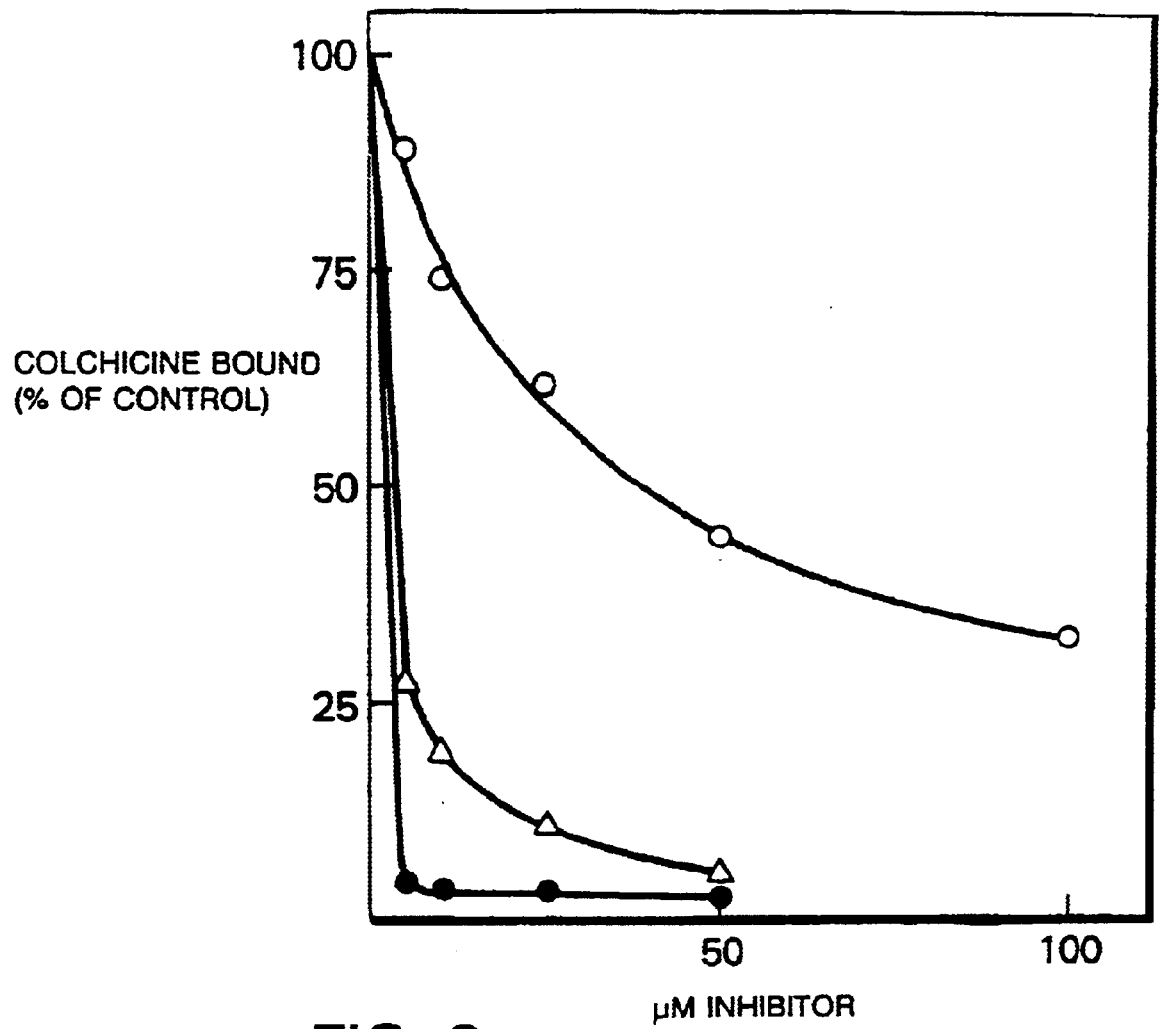
FIG. 2 is a graph illustrating the inhibition of colhicine binding to tubulin by 2-methoxyestradiol described by Example 2 below.

FIG. 2 illustrates that 2-methoxyestradiol inhibits colchicine binding to tubulin. Reaction conditions were as described in the text, with each reaction mixture containing 1.0 $\mu$M tubulin, 5% (v/v) dimethyl sulfoxide, 5 $\mu$M [$^3$H] colchicine, and inhibitor at the indicated concentrations. Incubation was for 10 min at 37° C. Symbols as follows: ○, 2-methoxyestradiol; ●, combretastatin A-4; ▲, dihydrocombretastatin A-4. Combretastatin A-4 and dihydrocombretastatin A-4 are compounds with anti-mitotic activity similar to colchicine.

EXAMPLE 4

Table 1 illustrates the inhibitory effects on tubulin polymerization in vitro exhibited by estradiol or estradiol derivatives, plant anti-mitotic compounds such as colchicine, combretastatin A-4 or other plant compounds. The method is given in Example 1.

EXAMPLE 5

Table 2 lists estrogens, estradiol or estradiol derivatives that inhibit colchicine binding to tubulin, by the method given in Example 3.

TABLE 1

| Estrogenic Compound | IC$_{50}$ ($\mu$M ± S.D.) |
|---|---|
| 2-Methoxyestradiol | 1.9 ± 0.2 |
| Diethylstilbestrol | 2.4 ± 0.4 |
| 2-Bromoestradiol | 4.5 ± 0.6 |
| 2-Methoxyestrone | 8.8 ± 1 |
| 17-Ethynylestradiol | 10.0 ± 2 |
| 2-Fluoroestradiol | 27.0 ± 6 |
| Estradiol | 30.0 ± 6 |
| Estrone | >40 |
| 2-Methoxy-17-ethynylestradiol | >40 |
| Estriol | >40 |
| 2-Methoxyestriol | >40 |
| Estradiol-3-O-methyl ether | >40 |

TABLE 1-continued

|  | IC$_{50}$ ($\mu$M ± S.D.) |
| --- | --- |
| 2-Methoxyestradiol-3-O-methyl ether | >40 |
| 4-Methoxyestradiol | >40 |
| 4-Methoxyestradiol-3-O-methyl ether | >40 |
| Plant Products | |
| Colchicine | 0.80 ± 0.07 |
| Podophyllotoxin | 0.46 ± 0.02 |
| Combretastatin A-4 | 0.53 ± 0.05 |
| Dihydrocombretastatin A-4 | 0.63 ± 0.03 |

IC$_{50}$ values are defined as the concentration of an estradiol derivative required to inhibit tubulin polymerization by 50%. IC$_{50}$ values were obtained in at least two independent experiments for non-inhibitory agents (IC$_{50}$>40 $\mu$M) and at least three independent experiments for inhibitory compounds. IC$_{50}$ values were obtained graphically, and average values are presented. S.D., standard deviation.

TABLE 2

| Estrogenic Compound | Percent inhibition ± S.D. |
| --- | --- |
| 2-Methoxyestradiol | 82 ± 2 |
| 2-Methoxyestrone | 57 ± 6 |
| 17-Ethynylestradiol | 50 ± 7 |
| Estradiol | 38 ± 4 |
| Diethylstilbestrol | 30 ± 4 |

Reaction conditions were described in Example 3, with each reaction mixture containing 1.0 $\mu$M tubulin, 5% (v/v) dimethyl sulfoxide, 2 $\mu$M [$^3$H]colchicine, and 100 $\mu$M inhibitor. Incubation was for 10 min at 37° C. Average values obtained in three independent experiments are presented in the table, except for 2-methoxyestrone, which was only examined twice. S.D., standard deviation.

What is claimed is:

1. A compound of the formula:

wherein:
I. $R_a$–$R_k$ are defined as follows:
  A) each $R_a$, $R_b$, $R_c$, $R_d$, $R_g$, $R_h$, $R_j$, $R_k$ independently is —$R_1$, —$OR_1$, —OCOR1, —$SR_1$, —F, —$NHR_2$, —Br, or —I; and $R_e$ is —$R_1$, —$OR_1$, —$OCOR_1$, —$SR_1$, —F, —$NHR_2$, —Br, —I or —C≡CH; or
  B) each $R_a$, $R_b$, $R_c$, $R_d$, $R_k$, independently is —$R_1$, —$OR_1$, $OCOR_1$, —$SR_1$, —F, —$NHR_2$, —Br, or —I; and each $R_g$, $R_h$, $R_i$, independently is =O, —$R_1$, —$OR_1$, —$OCOR_1$, —$SR_1$, —F, —Br, or —I; and $R_e$ is =O, —$R_1$, —$OR_1$, —$OCOR_1$, —$SR_1$, —F, —Br, —I or —C≡CH; and II. Z' is defined as follows:
  A) Z' is X, where X is >COR$_1$, >CC—R$_1$, >CC—OR$_1$, >CCH—R$_1$, >CCH—OR$_1$;
        ‖              ‖              |              |
        O              O              OH             OH B) Z' is =C—X'—    or    —X'—C=,
     |                    |
     R$_n$                 R$_n$ where $R_n$ is —$R_1$, —$OR_1$, —$Sr_1$, —F, —$NHR_2$, —Br, or —I;
  and X' is X, as defined above;
  or X' is >C=O; and III. Z" is defined as follows:
  A) Z" is —O—; or
  B) Z" is —O—CH—    or    —CH—O—,
        |                |
        R$_p$              R$_p$ where $R_p$ is —$R_1$, —$Or_2$, —$SR_1$, —F, —$NHR_2$, —Br or —I;
where, in each formula set forth above, each $R_1$ and $R_2$ independently is —H, or an alkyl, alkenyl or alkynyl group of up to 6 carbons.

2. A compound of the formula:

wherein:
I. $R_a$–$R_o$ are defined as follows:
  A) each $R_a$, $R_b$, $R_c$, $R_d$, $R_e$, $R_f$, $R_i$, $R_j$, $R_k$, $R_L$, $R_m$, $R_o$ independently is —$R_1$, —$OR_1$, —$OCOR_1$, —$SR_1$, —F, —$NHR_2$, —Br, or —I; and $R_g$ is —$R_1$, —$OR_1$, —$OCOR_1$, —$SR_1$, —F, —$NHR_2$, —Br, —I or —C≡CH; or
  B) each $R_a$, $R_b$, $R_c$, $R_f$, $R_k$, $R_L$, independently is —$R_1$, —$OR_1$, —$OCOR_1$, —$SR_1$, —F, —$NHR_2$, —Br, or —I; and each $R_d$, $R_e$, $R_i$, $R_j$, $R_m$, $R_O$ independently is =O, —$R_1$, —$OR_1$, —$OCOR_1$, —$SR_1$, —F, —$NHR_2$, —Br, —I; and $R_g$ is =O, —$R_1$, —$OR_1$, —$OCOR_1$, —$SR_1$, —F, —$NHR_2$, —Br, —I or —C≡CH; and II. Z is defined as follows:
  A) Z is —O—; or B) Z is —O—CH—    or    —CH—O—,
        |                |
        R$_n$              R$_n$ where $R_n$ is —$R_1$, —$OR_1$, —$SR_1$, —$NHR_2$, —Br or —I;
where, in each formula set forth above, each $R_1$ and $R_2$ independently is —H, or an alkyl, alkenyl or alkynyl group of up to 6 carbons.

3. A compound of the formula:

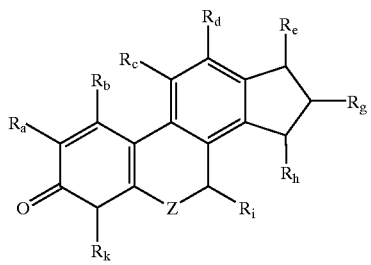

wherein:
I. $R_a$–$R_k$ are defined as follows:
  A) each $R_a$, $R_b$, $R_c$, $R_d$, $R_g$, $R_h$, $R_i$, $R_k$ independently is —$R_1$, —$OR_1$, —$OCOR_1$, —$SR_1$, —F, —$NHR_1$, —Br, or —I; and $R_e$ is —$R_1$, —$OR_1$, —$OCOR_1$, —$SR_1$, —F, —$NHR_1$, —Br, —I or —C≡CH; or
  B) each $R_a$, $R_b$, $R_c$, $R_d$, independently is —$R_1$, —$OR_1$, —$OCOR_1$, —$SR_1$, —F, —$NHR_1$, —Br, or —I; and each $R_g$, $R_h$, $R_i$, $R_k$ independently is =O, —$R_1$, $OR_1$, —$OCOR_1$, —$SR_1$, —F, —$NHR_1$, —Br or —I; and $R_e$ is —$R_1$, —$OR_1$, —$OCOR_1$, —$SR_1$, —F, —$NHR_1$, —Br, —I or —C≡CH; and
II. Z is defined as follows:
  A) Z is —O—; or B) Z is

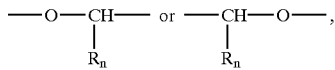

where $R_n$ is —$R_1$, —$OR_1$, —$SR_1$, —F, —$NHR_2$, —Br or —I;
where, in each formula set forth above, each $R_1$ and $R_2$ independently is —H, or an alkyl, alkenyl or alkynyl group of up to 6 carbons.

4. The compound of claim 1, wherein
  A) Z' is

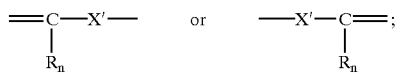

and Z" is

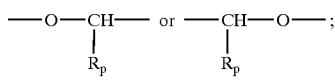

or

B) Z' is X; and Z" is

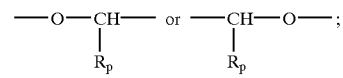

or
C) Z' is

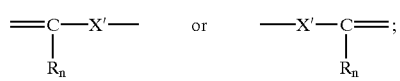

and Z" is —O—.

5. The compound of claim 2, wherein Z is

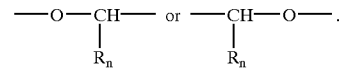

6. The compound of claim 3, wherein Z is

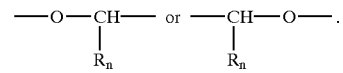

7. The compound of claim 1, wherein at least one of $R_a$ to $R_k$ is —$OCH_3$.

8. The compound of claim 2, wherein at least one of $R_a$ to $R_o$ is —$OCH_3$.

9. The compound of claim 3, wherein at least one of $R_a$ to $R_k$ is —$OCH_3$.

10. A method for treating a mammalian disease characterized by abnormal cell mitosis, comprising administering to a mammal the cell mitosis-inhibiting compound of claim 1, wherein the compound is administered in an amount sufficient to inhibit cell mitosis.

11. The method of claim 10, wherein $R_a$ is selected from —$OR_1$ or —$OCOR_1$.

12. A method for treating a mammalian disease characterized by abnormal cell mitosis, comprising administering to a mammal the cell mitosis-inhibiting compound of claim 2, wherein the compound is administered in an amount sufficient to inhibit cell mitosis.

13. The method of claim 12, wherein $R_a$ is selected from —$OR_1$ or —$OCOR_1$.

14. A method for treating a mammalian disease characterized by abnormal cell mitosis, comprising administering to a mammal the cell mitosis-inhibiting compound of claim 3, wherein the compound is administered in an amount sufficient to inhibit cell mitosis.

15. The method of claim 14, wherein $R_a$ is selected from —$OR_1$ or —$OCOR_1$.

* * * * *